(12) United States Patent
Drake et al.

(10) Patent No.: US 10,302,544 B2
(45) Date of Patent: May 28, 2019

(54) FLUIDIC DEVICE THAT EMULATES A FRACTURE IN A FORMATION AND IS USED TO TEST FLOW OF A TREATMENT FLUID THROUGH THE DEVICE

(71) Applicant: Halliburton Energy Services, Inc., Houston, TX (US)

(72) Inventors: Frederick L. Drake, Bossier City, LA (US); Jody M. Burks, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/573,404

(22) PCT Filed: Jun. 10, 2015

(86) PCT No.: PCT/US2015/035000
§ 371 (c)(1),
(2) Date: Nov. 10, 2017

(87) PCT Pub. No.: WO2016/200375
PCT Pub. Date: Dec. 15, 2016

(65) Prior Publication Data
US 2018/0156708 A1 Jun. 7, 2018

(51) Int. Cl.
*E21B 41/00* (2006.01)
*E21B 43/26* (2006.01)
(Continued)

(52) U.S. Cl.
CPC ......... *G01N 15/0826* (2013.01); *E21B 41/00* (2013.01); *E21B 43/26* (2013.01); *G01N 15/0806* (2013.01); *E21B 43/267* (2013.01)

(58) Field of Classification Search
CPC ........ E21B 41/00; E21B 43/26; E21B 43/267; G01N 15/0806; G01N 15/0826
See application file for complete search history.

(56) References Cited

U.S. PATENT DOCUMENTS

2013/0000895 A1 1/2013 Harold et al.
2014/0216149 A1 8/2014 Zhou et al.
(Continued)

FOREIGN PATENT DOCUMENTS

WO 2014193577 A1 12/2014

OTHER PUBLICATIONS

International Search Report and Written Opinion dated Mar. 2, 2016; International PCT Application No. PCT/US2015/035000.
(Continued)

*Primary Examiner* — James G Sayre
(74) *Attorney, Agent, or Firm* — McGuireWoods LLP (57) ABSTRACT

A fluidic device that can emulate a fracture is provided and includes a body with a first region that can emulate a propped fracture and a second region that can emulate an earth formation material. A test fluid flows into the device at a test pressure and temperature, and substantially fills the first and second regions. A portion of the test fluid flows back out of the device when the pressure is reduced. A method of emulating fluid flow through a fracture is provided, the method including a fluidic device that includes a body, a first region that emulates the fracture, and a second region that emulates an earth formation material. Flowing a test fluid at a test pressure and temperature into the first region, and reducing a pressure of the test fluid, thereby allowing some of the test fluid to flow from the device.

30 Claims, 10 Drawing Sheets (51) Int. Cl.
*G01N 15/08* (2006.01)
*E21B 43/267* (2006.01)

(56) References Cited

U.S. PATENT DOCUMENTS

2014/0290937 A1* 10/2014 Crews .................... E21B 43/26
166/250.1
2015/0066453 A1   3/2015 Bai et al.

OTHER PUBLICATIONS

Clean Technology Conference & Expo Jun. 13-16, 2011 Boston, MA; http://www.techconnectworld.com/Cleantech2011/.
Gunda, Naga Siva Kumar, et al. "Reservoir-on-a-Chip (ROC): A new paradigm in reservoir engineering." Lab on a Chip 11.22 (Jun. 27, 2011): 3785-3792.
He, Kai, et al. "Validating surfactant performance in the eagle ford shale: A correlation between the reservoir-on-a-chip approach and enhanced well productivity." SPE Improved oil recovery symposium. Society of Petroleum Engineers, 2014.

* cited by examiner

FLUIDIC DEVICE THAT EMULATES A FRACTURE IN A FORMATION AND IS USED TO TEST FLOW OF A TREATMENT FLUID THROUGH THE DEVICE

TECHNICAL FIELD

A fluidic device and methods for testing the flow of treatment fluids through a structure that is representative of a proppant filled fracture downhole in a wellbore. The device includes at least first and second regions, where the first region emulates a fracture in a subterranean earth formation, and the second region emulates the earth formation surrounding the fracture. By analyzing the flow of the treatment fluid(s) through the device, actual treatment fluids can be prepared to optimize the interaction and effectiveness of the treatment fluid in an actual wellbore. The device can also be used to estimate actual treatment fluids and possible proppant for a future wellbore. Therefore, it is not a requirement that the device exactly emulates a fracture or proppant filled fracture of a wellbore for which treatment fluid is being prepared. The earth formation material and the fracture parameters can be estimated from historical data, sensed data, and/or knowledge. According to certain embodiments, the fluidic device is used in oil or gas well test operations.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION

Oil and gas hydrocarbons are naturally occurring in some subterranean formations. In the oil and gas industry, a subterranean formation containing oil or gas is referred to as a reservoir. A reservoir may be located under land or off shore. Reservoirs are typically located in the range of a few hundred feet (shallow reservoirs) to a few tens of thousands of feet (ultra-deep reservoirs). In order to produce oil or gas, a wellbore is drilled into a reservoir or adjacent to a reservoir. The oil, gas, or water produced from a reservoir is called a reservoir fluid. As used herein, a "fluid" is a substance having a continuous phase that tends to flow and to conform to the outline of its container when the substance is tested at a temperature of 71° F. (22° C.) and a pressure of one atmosphere "atm" (0.1 megapascals "MPa"). A fluid can be a liquid or gas.

A well can include, without limitation, an oil, gas, or water production well, or an injection well. As used herein, a "well" includes at least one wellbore. A wellbore can include vertical, inclined, and horizontal portions, and it can be straight, curved, or branched. As used herein, the term "wellbore" includes any cased, and any uncased, open-hole portion of the wellbore. The well can also include multiple wellbores, such as a main wellbore and lateral wellbores. As used herein, the term "wellbore" also includes a main wellbore as well as lateral wellbores that branch off from the main wellbore or from other lateral wellbores. A near-wellbore region is the subterranean material and rock of the subterranean formation surrounding the wellbore. As used herein, a "well" also includes the near-wellbore region. The near-wellbore region is generally considered to be the region within approximately 100 feet radially of the wellbore. As used herein, "into a well" means and includes into any portion of the well, including into the wellbore or into the near-wellbore region via the wellbore.

In an open-hole wellbore portion, a tubing string may be placed into the wellbore. The tubing string allows fluids to be introduced into or flowed from a remote portion of the wellbore. In a cased-hole wellbore portion, a casing is placed into the wellbore that can also contain a tubing string. A wellbore can contain an annulus. Examples of an annulus include, but are not limited to: the space between the wellbore and the outside of a tubing string in an open-hole wellbore; the space between the wellbore and the outside of a casing in a cased-hole wellbore; and the space between the inside of a casing and the outside of a tubing string in a cased-hole wellbore.

It is not uncommon for a wellbore to extend several hundreds of feet or several thousands of feet into a subterranean formation. The subterranean formation can have different zones. A zone is an interval of rock differentiated from surrounding rocks on the basis of its fossil content or other features, such as faults or fractures. For example, one zone can have a higher permeability compared to another zone. Each zone of the formation can be isolated within the wellbore via the use of packers or other similar devices.

It is often desirable to produce a reservoir fluid from multiples zones of a formation. Due to differences in the earth formations surrounding the various zones and/or differences in reservoir pressures at these different zones, some zones may not produce sufficient amounts of reservoir fluids to economically maintain production. The zones can be perforated to increase production, and this may provide adequate fluid production for a period of time. However, the zones may again supply insufficient fluid production after being perforated. Therefore, it can be desirable to further stimulate the earth formations in these zones by injecting a treatment fluid into the earth formation through the perforations to enhance production or use the treatment fluid to perform fracturing operations on these zones which increase permeability of the zones, thereby enhancing fluid production.

A fracturing fluid, often called a pad fluid, is pumped using a frac pump at a sufficiently high flow rate and high pressure into the wellbore and into the subterranean formation to create or enhance a fracture in the subterranean formation. Creating a fracture means making a new fracture in the formation. Enhancing a fracture means enlarging a pre-existing fracture in the formation. As used herein, the term "fracture" means the creation or enhancement of a natural fracture using a fracturing fluid, and can be referred to as "man-made." To fracture a subterranean formation typically requires hundreds of thousands of gallons of fracturing fluid. Further, it is often desirable to fracture at more than one downhole location. Therefore, the base fluid of a fracturing fluid is usually water or water-based for various reasons, including the ready availability of water and the relatively low cost of water compared to other liquids.

The newly-created or enhanced fracture will tend to close together after pumping of the fracturing fluid has stopped due to the weight of the subterranean formation. To prevent the fracture from closing, a material must be placed in the fracture to keep the fracture propped open. A material used for this purpose is often referred to as a "proppant." The proppant is in the form of solid particles, which can be suspended in the fracturing fluid, carried down hole, and deposited in the fracture as a "proppant pack." The proppant pack generally props the fracture in an open position while allowing fluid flow through the permeability of the pack.

Proppant materials generally include silicon dioxide, walnut shells, sintered bauxite, glass, plastics, ceramic materials, and any combination thereof in any proportion. The proppant is an appropriate size to prop open the fracture and allow fluid to flow through the proppant pack, that is, in between and around the proppant making up the pack. Appropriate sizes of particulate for use as a proppant are typically in the range from about 8 to about 100 U.S. Standard Mesh. A typical proppant is sand-sized, which geologically is defined as having a largest dimension ranging from 0.0625 millimeters up to 3 millimeters.

The subterranean formation will exert a force or pressure on the proppant located within the fracture. This is known as the closure stress of the formation or fracture. The proppant is generally sufficiently strong, that is, have a sufficient compressive or crush resistance, to prop the fracture open without being deformed or crushed by the closure stress of the fracture. Pressures from the subterranean formation on the proppant located in the fractures can be as high as 10,000 to generally 15,000 or more pounds force per square inch (psi). If a proppant material crushes under closure stress, then the fracture will close and no longer function to provide a less restrictive fluid flow path for production of reservoir fluids. As such, proppant generally has a crush resistance measured as less than about 5% to 10% of the proppant crushes under the closure stress of the formation. Accordingly, about 90% to 95% of the proppant does not crush under the closure stress and functions to keep the fracture in an open position. The proppant must generally be a high-quality proppant and the size and shape of the proppant selected to provide the desired crush resistance.

The conductivity of the fracture (i.e., the flow rate of fluid through the fracture) and the duration of the conductivity is related to the quality of the proppant, the size of the proppant, and the placement of the proppant within the fracture. In order to increase the conductivity and conductivity life, higher-quality proppant is commonly used. The proppant can be placed within the fracture such that the top part of the fracture has approximately the same amount of permeability as the bottom part of the fracture. However, the proppant can also be placed in the fracture with varying permeability of the resulting proppant pack.

The treatment fluids include a base fluid. As used herein, the term "base fluid" means the liquid that is in the greatest concentration and is the solvent of a solution or the continuous phase of a heterogeneous fluid. The base fluid can include water. The water can be selected from the group consisting of fresh water, brackish water, sea water, brine, produced water—as it is or processed, and any combination thereof in any proportion. The treatment fluids can also include water-miscible liquids, hydrocarbon liquids, and gases.

The treatment fluids can contain various additives, such as surfactants, gel stabilizers, anti-oxidants, polymer-degradation-prevention additives, relative-permeability modifiers, corrosion inhibitors, foaming agents, defoaming agents, antifoaming agents, emulsifying agents, de-emulsifying agents, iron control agents, particulate diverters, salts, acids, fluid-loss-control additives, gas, catalysts, clay control agents, dispersants, flocculants, scavengers (e.g., $H_2S$ scavengers, $CO_2$ scavengers, or $O_2$ scavengers), gelling agents, lubricants, breakers, friction reducers, bridging agents, viscosifiers, weighting agents, solubilizers, pH control agents (e.g., buffers), hydrate inhibitors, consolidating agents, bactericides, catalysts, clay stabilizers, breakers, delayed-release breakers, and combinations thereof.

The treatment fluids can also include proppant (e.g., when the treatment fluid is used for fracturing). The proppant can be selected from the group consisting of nut shells, sand, ceramics, natural sand, quartz sand, particulate garnet, metal particulates, glass, nylon pellets, bauxite and other ores, polymeric materials, and combinations thereof in any proportion. The proppant can be substantially spherical in shape, fibrous materials, polygonal shaped (such as cubic), irregular shapes, and any combination thereof. A surface modification agent can be coated onto the proppant.

The proppant can also be coated with a curable resin or tackifying agent. The curable resin or tackifying agent can help the proppant form a proppant pack within the fracture. The curable resin can be part of a curing resin system. The curable resin can be any compound that is capable of curing (i.e., the process of gaining compressive strength and becoming hard). The curable resin can cure via a chemical reaction with a curing agent or via temperature. The curable resin can coat the proppant prior to or during introduction of the fracturing fluid into the well. The curable resin can also chemically bond with the surfaces of the proppant. According to certain embodiments, the curable resin is an epoxy, diepoxy, polyepoxy resin, phenol-formaldehyde, or furan-based resin. For example, the curable resin can be bisphenol A glycidyldiepoxy, glycidyl propyltrimethoxysilane. The curable resin can be in a concentration in the range of about 0.1% to about 10% by weight of the resin system.

Accordingly, a wide range of treatment fluids can be used to stimulate or fracture the particular zones, as well as widely varying the proportions of any additives included in the treatment fluids. This creates an almost unlimited amount of variations that are possible when preparing a specific treatment fluid for a particular wellbore or zone. Therefore, when a treatment fluid is prepared for a particular earth formation, it is very beneficial to test the fluid's performance on a material that is representative of the particular earth formation prior to treating the wellbore or zone. As used herein "representative" means that the item emulates, mimics, or otherwise closely approximates the properties of the item being represented. The representative material can be actual cuttings from the wellbore, core samples from the wellbore or a similar wellbore, a material that closely approximates the earth formation material, an estimated material based on historical data, sensed data, and/or knowledge, etc.

Currently, a test environment is setup in a lab at a remote location from the well site to test the performance of the treatment fluid and make any modifications to the treatment fluid to optimize its performance with the representative material. A "column flow test" (i.e., liquid chromatography)

is commonly used to test the flow rate of the treatment fluid through the representative material that fills a portion of a tube. The test treatment fluid is introduced through the representative material, displaced by liquid hydrocarbons or gas, and is collected from the bottom of the tube. The fluid is then analyzed for the amount of displacement, flow rate, and/or total amount of fluid collected.

Additionally, treatment fluids can be required to flow through proppant packs of fractures to stimulate and/or further fracture the earth formation in the wellbore or zone. This further complicates modeling and/or testing of treatment fluid performance in the wellbore because at least two different regions of material (e.g., earth formation material and proppant material) must be included in the treatment fluid testing to more accurately assess performance of the treatment fluid. Unfortunately, conditions (such as pressure and temperature) in the laboratory are not able to fully represent the downhole conditions of the wellbore or zone. This can negatively affect the validity of the testing because the treatment fluid can react differently to the earth formation and possible proppant at the pressure differentials and temperatures of a predetermined downhole location in the subterranean earth formation that surrounds a wellbore.

It has been discovered that a fluidic device can be manufactured to emulate the multiple material regions of a wellbore fracture, provide flow testing of the treatment fluid at conditions that are representative of the pressures (or at least pressure differentials) and temperatures of the predetermined downhole location in the wellbore, and provide portability allowing the device to be setup on-site at the well, thereby providing near real-time results (i.e., within a few hours to a few days). As used herein, a "predetermined downhole location" includes an actual location in a wellbore, and/or a proposed location in a future wellbore which has yet to be formed. Therefore, the device can be used to estimate treatment fluids to be used on an existing, modified, or proposed wellbore.

According to a certain embodiment, a fluidic device can be used to emulate a fracture in a subterranean earth formation (whether the fracture and/or the subterranean earth formation is hypothetical or real). The device can include a body, a first region that emulates the fracture, and a second region that emulates an earth formation material, where the first and the second regions are contained within the body of the device, and where the first region is in fluid communication with the second region. The device can also include a first port that is in fluid communication with the first region, and a second port that is in fluid communication with the second region, where a test treatment fluid, at elevated test pressure and temperature, flows into the device through the first port, and at least a portion of the test treatment fluid flows back out of the device when the pressure at the first port is reduced.

According to another certain embodiment, a method of emulating fluid flow through a fracture in a wellbore is provided. The method can include the step of constructing a fluidic device that includes a body, a first region that emulates the fracture, and a second region that emulates an earth formation material. The method can also include the steps of flowing a test treatment fluid at elevated test pressure and temperature into the first region via a first port, where the test pressure is elevated above a pressure that is representative of conditions at a predetermined downhole location in the subterranean earth formation, and where the test temperature is representative of temperatures at the predetermined location, and reducing the test pressure of the test treatment fluid at the first port, thereby allowing at least a portion of the test treatment fluid to flow out of the device.

According to another certain embodiment, a method of emulating fluid flow through a fracture in a subterranean earth formation. The method can include the step of constructing a fluidic device that includes a body, a first region that emulates a fracture, second and third regions that emulate an earth formation material, and a fourth region that emulates adsorption characteristics of the earth formation material. The method can include the steps of flowing a test treatment fluid at elevated test pressure and temperature into the device via a first port, through the fourth region, and into the first region, where the test pressure is elevated above a pressure that is representative of conditions at a predetermined downhole location in the subterranean earth formation, and where the test temperature is representative of temperatures at the predetermined location, supplying a representative formation fluid to the second and third regions via second and third ports, respectively, creating a desired backpressure in the device by preventing fluid from flowing out of the device via a fourth port positioned on a side of the first region opposite the first port, then permitting fluid flow from the device via the fourth port, and analyzing the fluid that flows from the fourth port, analyzing the adsorption by the fourth region of additives in the test treatment fluid, and creating an actual treatment fluid and/or a treatment system based on the results of the analyzing steps. The fluid may also be analyzed at various stages of the fluidic device, such as before and/or after flowing through the fourth region, between the fourth and first region injection, and after displacement out of the device by a formation fluid.

Any discussion of the embodiments regarding the fluidic device or any component related to the fluidic device is intended to apply to all of the apparatus and method embodiments.

Figure 1:
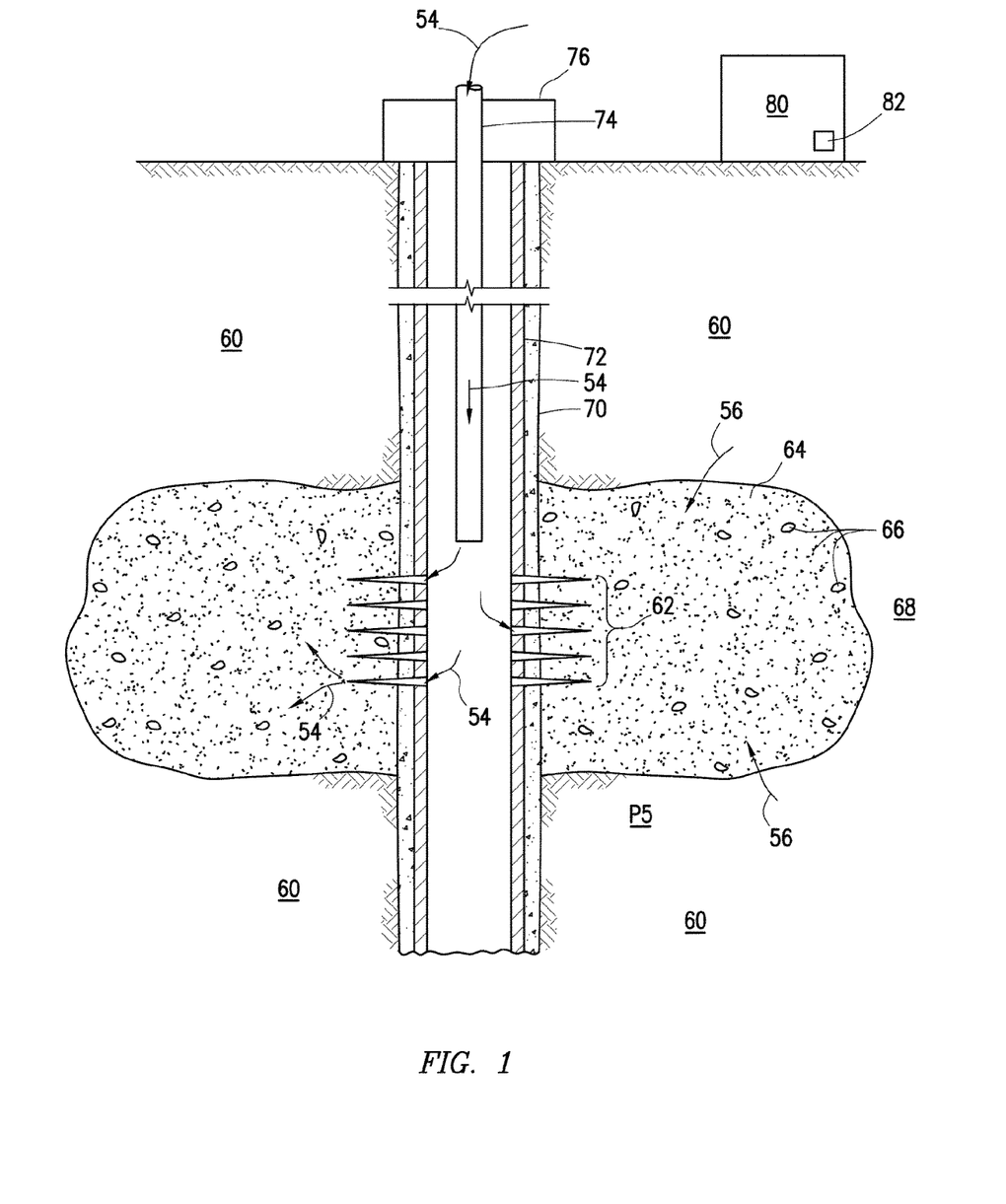
FIG. 1 depicts a partial cross-sectional view of a cased wellbore with perforations and a fractured earth formation.

Turning to the Figures, FIG. 1 depicts a partial cross-sectional view of an example of a wellbore 70 with a wellhead 76 and a casing 72. An on-site testing facility 80 is also shown with a semi-automated or automated selection device 82 included in the facility 80. A zone 68 is shown with a downhole pressure P5 in the earth formation. The earth formation 60 can also be at a higher temperature than the temperature at the surface. The zone 68 has been fractured by pumping a treatment fluid 54 (e.g., a fracturing fluid) into the perforations 62 at high pressure and high volume, thereby forming the fracture 64 and filling the fracture 64 with proppant 66 to prevent the fracture 64 from closing after it has been opened during the fracturing process. However, before the fracturing process is performed, testing the treatment fluid 54 is desired to ensure that the treatment fluid 54 is prepared with the proper base fluid and the proper additives to successfully develop a fracture 64 that enhances formation fluid 56 production.

Figure 2:
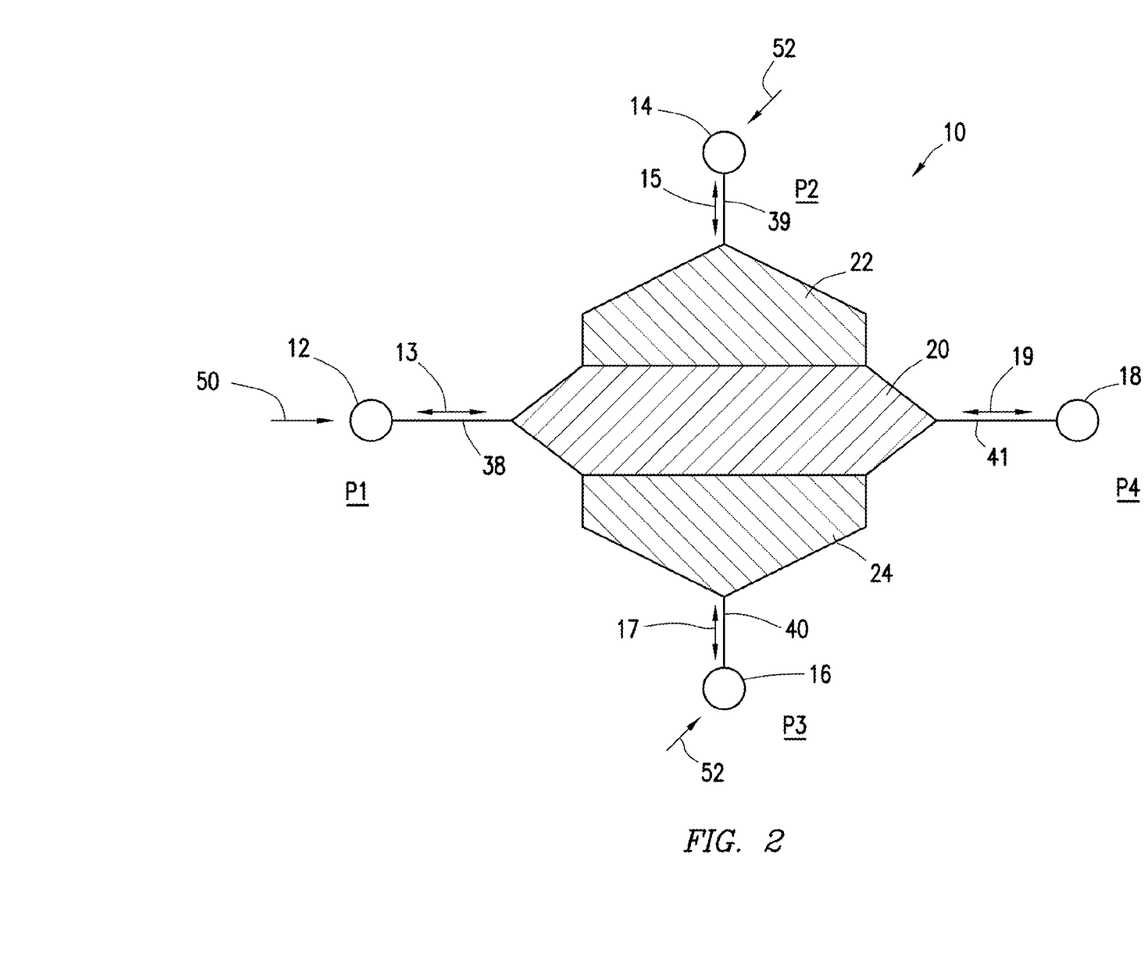
FIGS. 2-5 depict schematic diagrams of flow paths of a fluidic device according to certain embodiments.

Referring now to FIG. 2, it depicts a schematic representation of possible flow passages 10 in a fluidic device 30 (see FIG. 6) that can be used to test the flow performance of a test treatment fluid 50 through a proppant 66 filled fracture 64 in a subterranean formation 70. The flow passages 10 can include first, second, and third regions 20, 22, 24 that emulate the pore structures of the proppant 66 filled fracture 64. The first region 20 can emulate the fracture 64 that may contain actual proppant material 66, by filling the first region 20 with the actual proppant material 66, or forming the region 20 by using lithography, etching (such as chemical, physical, laser, etc.), 3D printing, 3D powder printing, cutting, milling, and/or stamping to produce the desired flow channels through the region 20. It should be understood that the fracture 64 may not contain proppant material 66, and that the fluidic device 30 can emulate the fracture 64 when proppant material 66 is not contained within the fracture 64. These flow channels can emulate the flow channels of the actual proppant material 66 as the channels would be when the proppant 66 is packed in the fracture 64 during the fracturing process, or the flow channels can emulate the flow channels of the fracture 64 when proppant 66 is not contained within the fracture. The second region 22 can emulate the earth formation material 60 that is to be fractured in the fracturing process by filling the second region 22 with the actual earth formation material 60, or forming the second region 22 by using lithography, etching (such as chemical, physical, laser, etc.), 3D printing, 3D powder printing, cutting, milling, and/or stamping to produce the desired flow channels through the second region 22. These flow channels can emulate the flow channels of the actual earth formation material 60. The geometries of the flow channels through the fracture 64 and the earth formation material 60 can be determined by several means, such as micro-computed tomography, focused ion beam-scanning electron microscope, nuclear magnetic resonance imaging, ultrasonic scanning, using the actual material, using a knowledge base, etc.

The flow passages 10 can also include a third region 24 that emulates the earth formation material 60 by filling the third region 24 with the actual earth formation material 60, or forming the region 24 by using lithography, etching (such as chemical, physical, laser, etc.), 3D printing, 3D powder printing, cutting, milling, and/or stamping to produce the desired flow channels through the third region 24. With the first region 20 positioned between the second and third regions 22, 24, the flow passages 10 of the fluidic device 30 can very closely emulate the flow passages of the fracture 64 that extend from the wellbore 70 in the earth formation material 60. The design of the flow passages 10 and the test treatment fluid 50 can be selected by use of an automated selection device 82 (such as a computer programmed with a database tool) by selecting the most closely related fracture properties, proppant, formation mineralogy and fluid chemistry.

FIG. 2 shows four fluid ports 12, 14, 16, 18 used to supply fluid to and/or receive fluid from the device 30. The possible flow directions to and from the ports 12, 14, 16, 18 are shown by arrows 13, 15, 17, 19. The pressures at each of the ports 12, 14, 16, 18 are indicated as P1, P2, P3, P4. Note that FIG. 1 indicates the pressure at the predetermined downhole location in the wellbore to be P5. The first fluid port 12, is connected to one side of the first region 20 by a first flow path 38. During a flow test, the test treatment fluid 50 can be injected into the port 12, flow through the first flow path 38 to the first region 20 and fill the region 20. The fluid 50 may also fill the second and third regions 22, 24 during the flow test. During the injection of the fluid 50 into the flow passages 10, the fourth port 18 can be used to maintain a desired backpressure in the flow passages 10. This allows the flow test to be performed at the representative downhole pressure P5. However, it is not necessary that the test be performed at the pressure levels of the predetermined downhole location. The test may also be performed by emulating the representative pressure differentials of the predetermined downhole location. Therefore, the pressures at each of the ports 12, 14, 16, 18 can be at reduced pressure levels from the actual pressure levels at the predetermined downhole location, but the pressure differentials across the device during the testing should at least be indicative of the actual pressure differentials, such as the pressure differentials between pressure P1 and either one of pressures P2 and P3.

A test formation fluid 52 can be supplied to the second and third ports 14, 16 at pressures P2, P3, where these pressures would preferably be substantially equal to pressure P5, or at least at pressures that produce pressure differentials indicative of the predetermined downhole location. The test formation fluid 52 can be oil, condensate, natural gas, etc. Therefore, pressure P1 at the first port 12 will be elevated above pressure P5 to force the test treatment fluid 50 into the flow passages 10. As the fluid 50 enters the flow passages 10, it fills at least a portion of the regions 20, 22, 24. When that fourth port 18 is opened to release some of the test treatment fluid 50, the fluid 50 can move through the flow passages 10 under a substantially constant controlled force by the fluid supplied to the ports 12, 14, 16 at pressures P1, P2, P3. The fluid 50 received from port 18 is analyzed to determine the resulting characteristics of the test treatment fluid 50 after it has passed through the flow passages 10. From this analysis a fracturing fluid recovery value can be captured, a breakthrough time of the fluid 50 can be determined, resulting concentrations of additives remaining in the received fluid 50 can be determined (providing adsorption rate values), etc. From the test results, the test treatment fluid 50 may be modified to improve the performance of the fluid 50. When the performance of the test treatment fluid is deemed acceptable, then an actual treatment fluid 54 can be prepared based on the resulting test treatment fluid 50, and the actual treatment fluid 54 can then be injected into the wellbore 70 to produce the fractures 64 in the earth formation 60 at zone 68. The testing of the test treatment fluid 50 at conditions representative of the actual location in the wellbore 70 ensures that the performance of the actual treatment fluid 54 will more closely agree with the test results from the fluidic device 30. However, it should be clearly understood that the actual treatment fluid that is prepared based on the resulting test treatment fluid can also be used on a wellbore other than wellbore 70. The other wellbore can be a future wellbore not yet formed in an earth formation.

Figure 3:
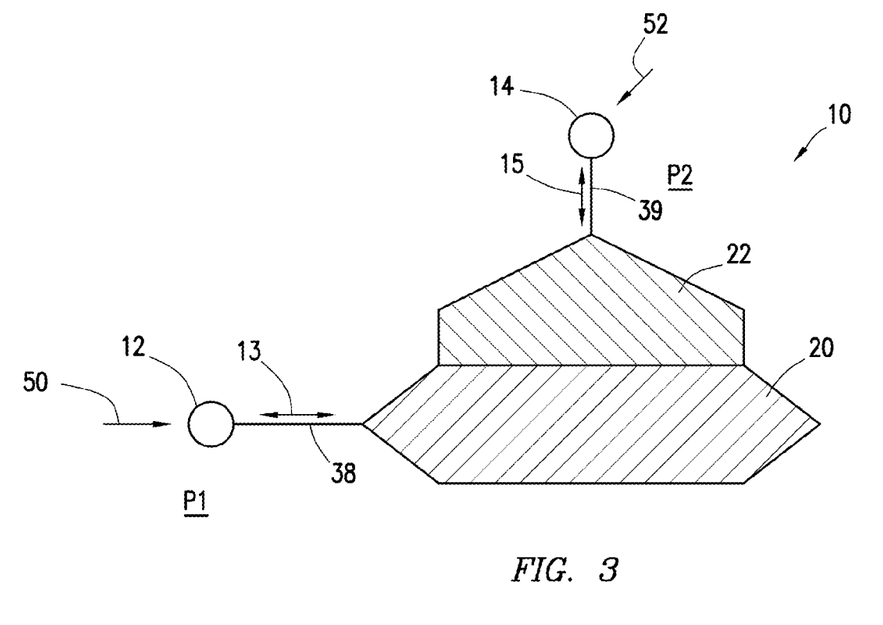

Referring now to FIG. 3, this figure shows that it is not necessary for the flow passages 10 of the device 30 to have all four ports or all three regions as shown in FIG. 2. FIG. 3 shows a first port 12 that can be used to supply test treatment fluid 50 to the flow passages 10, and a second port 14 that can be used to supply the test formation fluid 52 at pressure P2. Ports 16, 18 are not included in this certain embodiment. FIG. 3 also does not include the third region 24. Using this configuration of the flow passages 10, a flow test can be performed by supplying test formation fluid 52 to the second port 14 at a pressure P2, which is representative of pressure P5 in the wellbore 70. Then supplying test treatment fluid 50 to the first port 12 at a pressure P1 that is elevated with respect to pressure P2. This forces test treatment fluid 50 at least partially into the regions 20, 22 and displaces the test formation fluid at least partially from these regions. Then the pressure P1 can be reduced to be lower than pressure P2 which causes the test treatment fluid 50 that flowed into the flow passages 10 to be forced back out the first port 12. Flow directions of the test fluid 50 is shown by arrows 13. The test treatment fluid 50 received from the flow passages 10 is then tested to determine the performance of the test treatment fluid 50 with the emulated pore structure of the zone 68 in the wellbore 70 and with the desired proppant material 66 in the fracture 64 (if proppant is included in the fracture 64).

Figure 4:
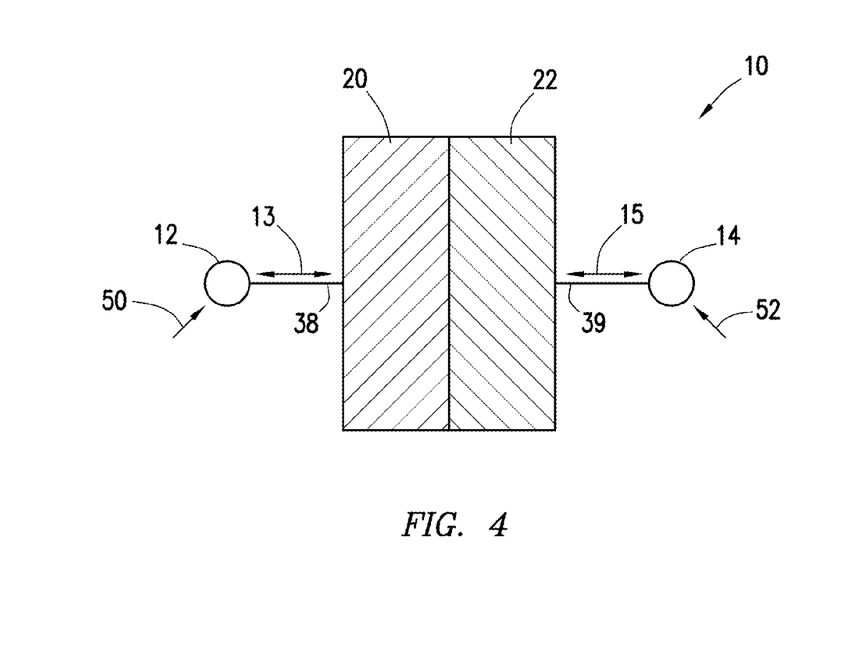

Referring now to FIG. 4, this figure is very similar in operation to the flow passages 10 shown in FIG. 3. However, FIG. 4 differs from FIG. 3 in that the flow of the test treatment fluid is generally right and left with respect to the figure. Other than this difference, the flow passages 10 shown in FIG. 4 work the same as the flow passages 10 of FIG. 3.

Figure 5:
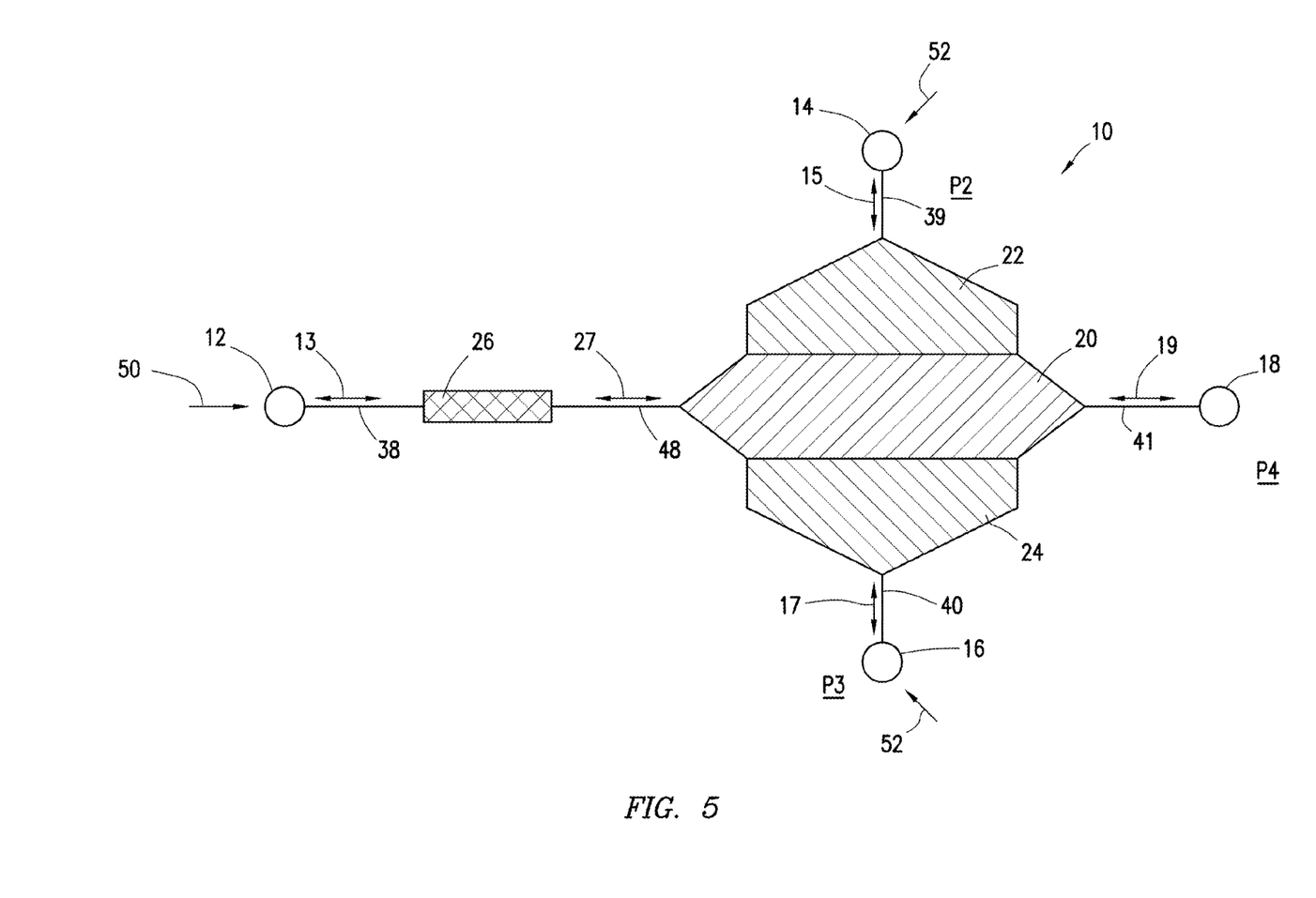

Referring now to FIG. 5, this figure is very similar to the configuration of the flow passages 10 in FIG. 2 in that it includes the first, second, and third regions 20, 22, 24 and all four ports 12, 14, 16, 18. However, this configuration also includes a fourth region 26 that is positioned between the first port 12 and the first region 20. The first port 12 supplies test treatment fluid 50 at pressure P1 to the first flow path 38, which supplies the fluid 50 to the fourth region 26. The fluid 50 flows through the fourth region 26 and to the first region 20 via a fifth flow path 48. This fourth region 26 can be used to emulate adsorption of additives in the test treatment fluid 50 as it passes through the region 26. The region 26 can emulate the earth formation material 60, or the proppant material, or combinations of the two by filling the region 26 with actual earth formation material 60 retrieved from the wellbore, such as through retrieved cuttings, core samples, etc., actual proppant material 66, or combinations of the formation and proppant materials.

The fourth region 26 can be loaded with actual or simulated material (earth formation material 60, proppant 66, or combinations thereof) through the use of a port, trap-door or by making the channel chamber itself a removable/reusable module. The module (not shown) can be used to pre-pack the region 26 using formation brine, sealed and inserted into the region 26. The module can be 3D printed using powder print technology. In such a case, actual or simulated materials could be ground to a powder of sufficient size and printed into a structure using a compatible inorganic binder. Compatibility of the inorganic binder can refer to having appropriate surface properties that do not distort with the resulting properties of additives (e.g., surfactants) in the test treatment fluid 50. This region 26 may be desired when the actual material for the earth formation 60 or the proppant 66 is not used in regions 20, 22, 24. Processes such as 3D printing, etching, etc. can provide the pore structures of the materials 60, 66, but may not adequately provide the adsorption properties of the materials 60, 66. Therefore, with the addition of regions 26, the adsorption portion of the testing can be maintained. However, it is not a requirement to include the fourth region 26 when performing flow tests on the test treatment fluids 50.

Figure 6:
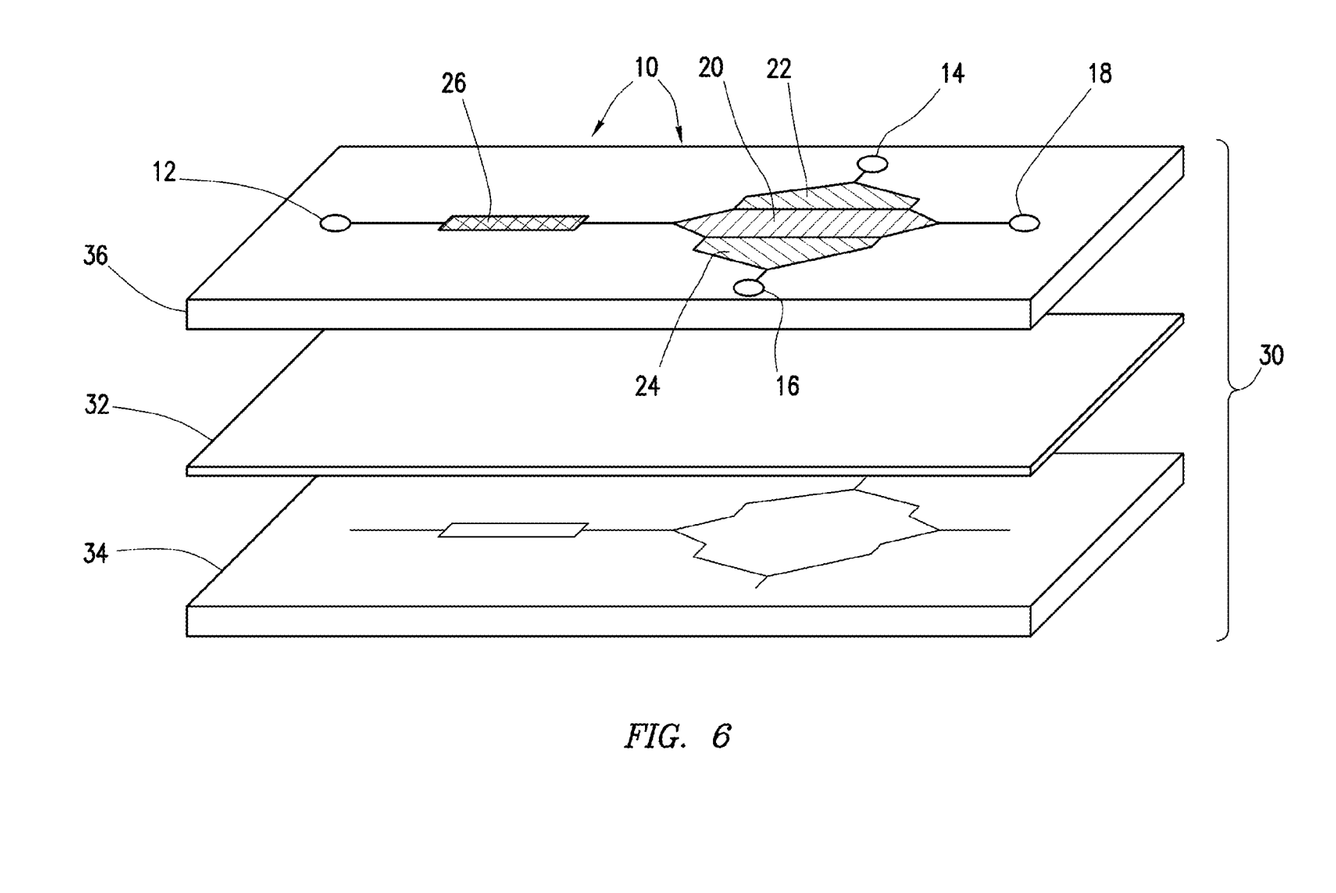
FIG. 6 depicts flow paths of a fluidic device formed in a substrate with a cover positioned between the substrate and a heater according to certain embodiments.
Figure 10:
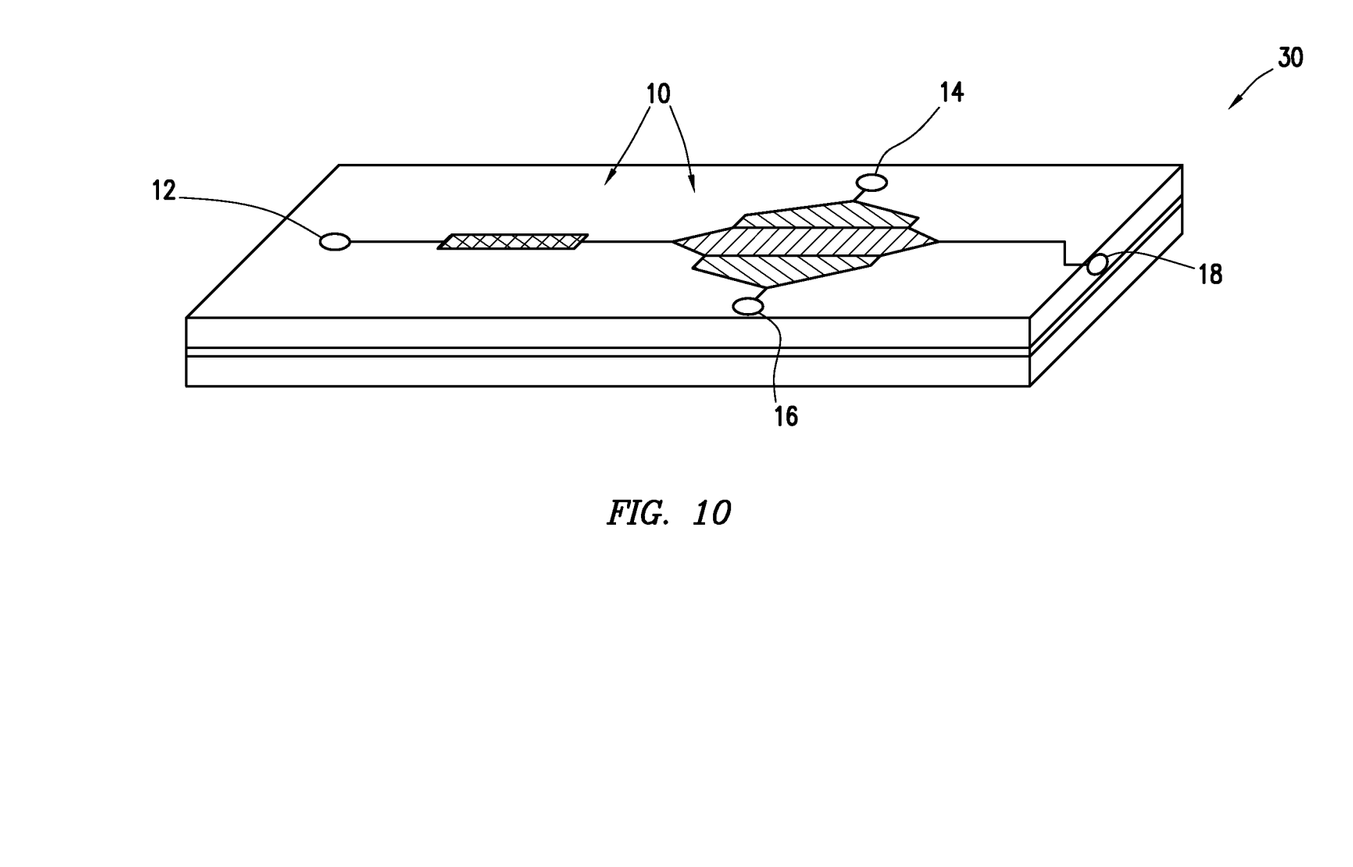
FIG. 10 depicts flow paths of a fluidic device formed in a substrate with one of the fluid ports formed in an end of the substrate according to certain embodiments.

Referring now to FIG. 6, this figure depicts the flow passages 10 shown in FIG. 5 to be manufactured on a substrate or body 36. It is preferable that the regions are formed in a clear body 36 and on the side of the body 36 that faces the cover 32. Therefore, the flow passages 10 in FIG. 6 are seen because they are formed into a clear body 36. The body 36 with the formed flow passages 10 can be assembled to a cover 32 that is also a clear material, such as glass. However, the cover 32 and the body 36 should be able to withstand the representative pressures (or at least representative pressure differentials) of the downhole location in the wellbore. Alternatively, a planar heater 34 may also be assembled into the fluidic device 30 in order to simulate the elevated temperatures of the predetermined downhole location. However, the heater 34 is optional and is not required for operation of the device 30. The ports 12, 14, 16, 18 are shown as holes through the body to provide connection to the flow paths 38, 39, 40, 41 (see FIG. 2). These ports may also be provided in the end or sides of the body 36. It is not required that the ports are connected on the top surface as shown in FIGS. 5-9. FIG. 10 shows port 18 formed in the end of the body 36. Many other connection orientations are also possible for routing the fluid through the device 30.

Figure 7:
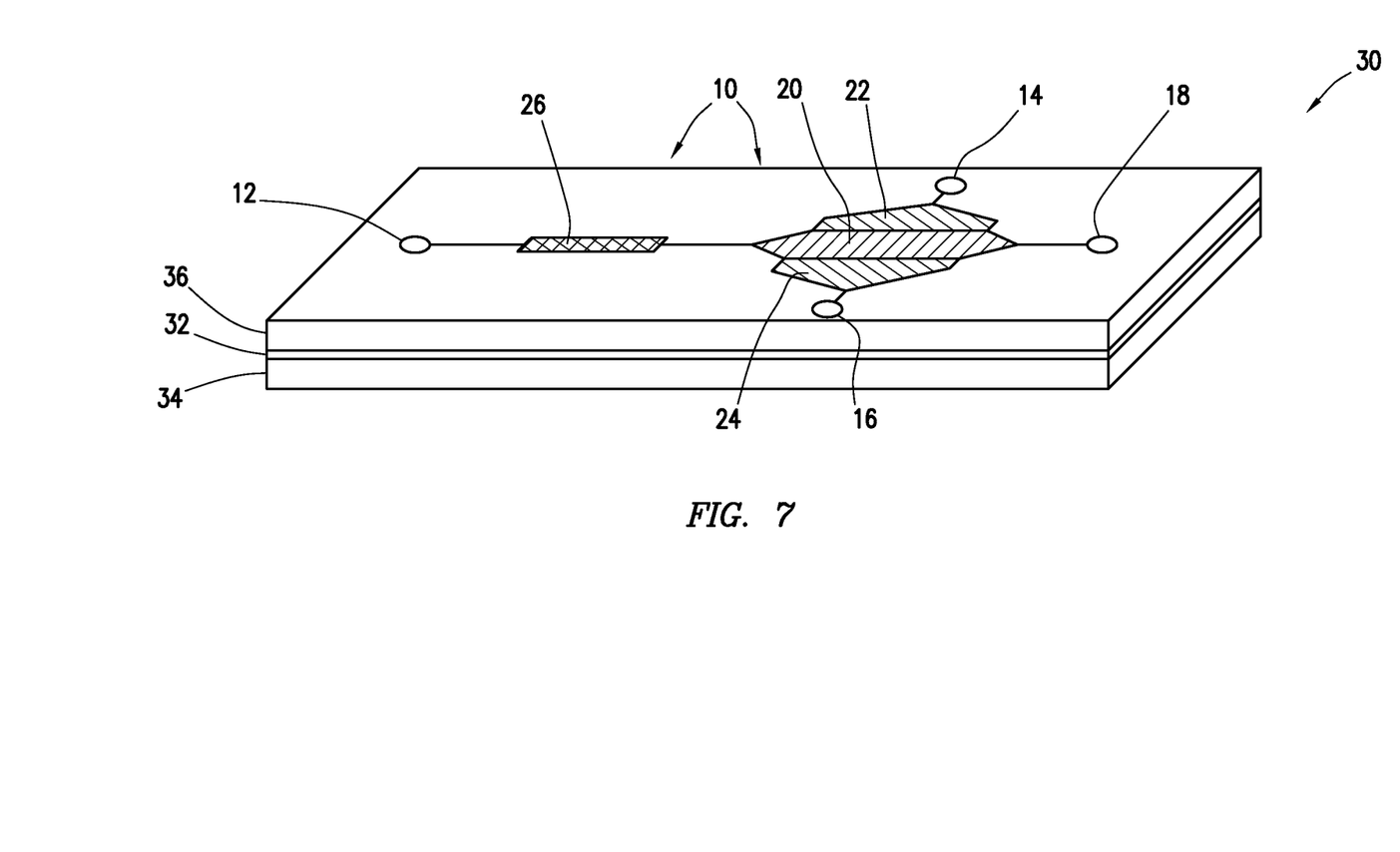
FIG. 7 depicts the fluidic device of FIG. 5 assembled together according to certain embodiments.
Figure 8:
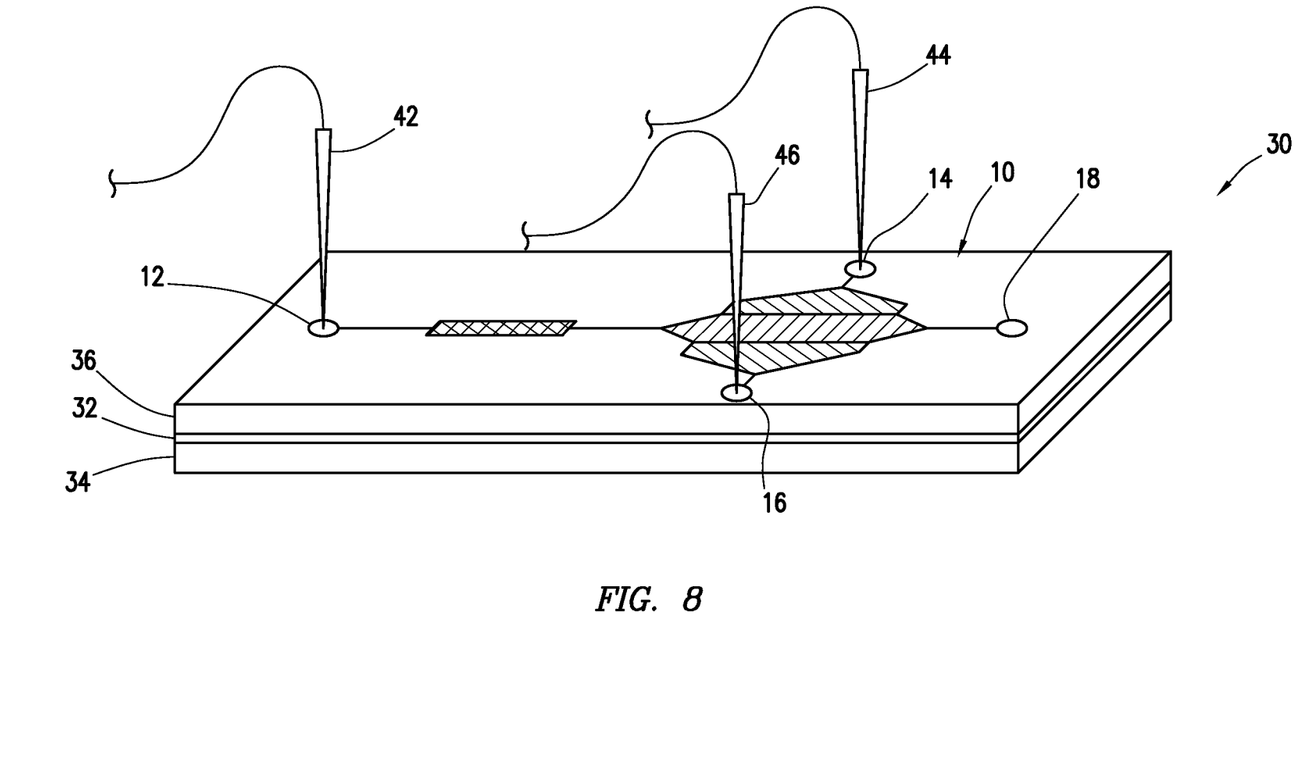
FIG. 8 depicts fluid probes connecting to fluid ports of the fluidic device of FIG. 6.

Referring now to FIGS. 7 and 8, FIG. 7 shows the fluidic device 30 of FIG. 6 assembled together. FIG. 8 shows possible connections of fluid probes 42, 44, and 46 to the ports 12, 14, 16. A similar connection can also be made to port 18, or other connections know to those skilled in the art can be used to provide fluid flow and pressure containment for the fluids used in the testing.

Figure 9:
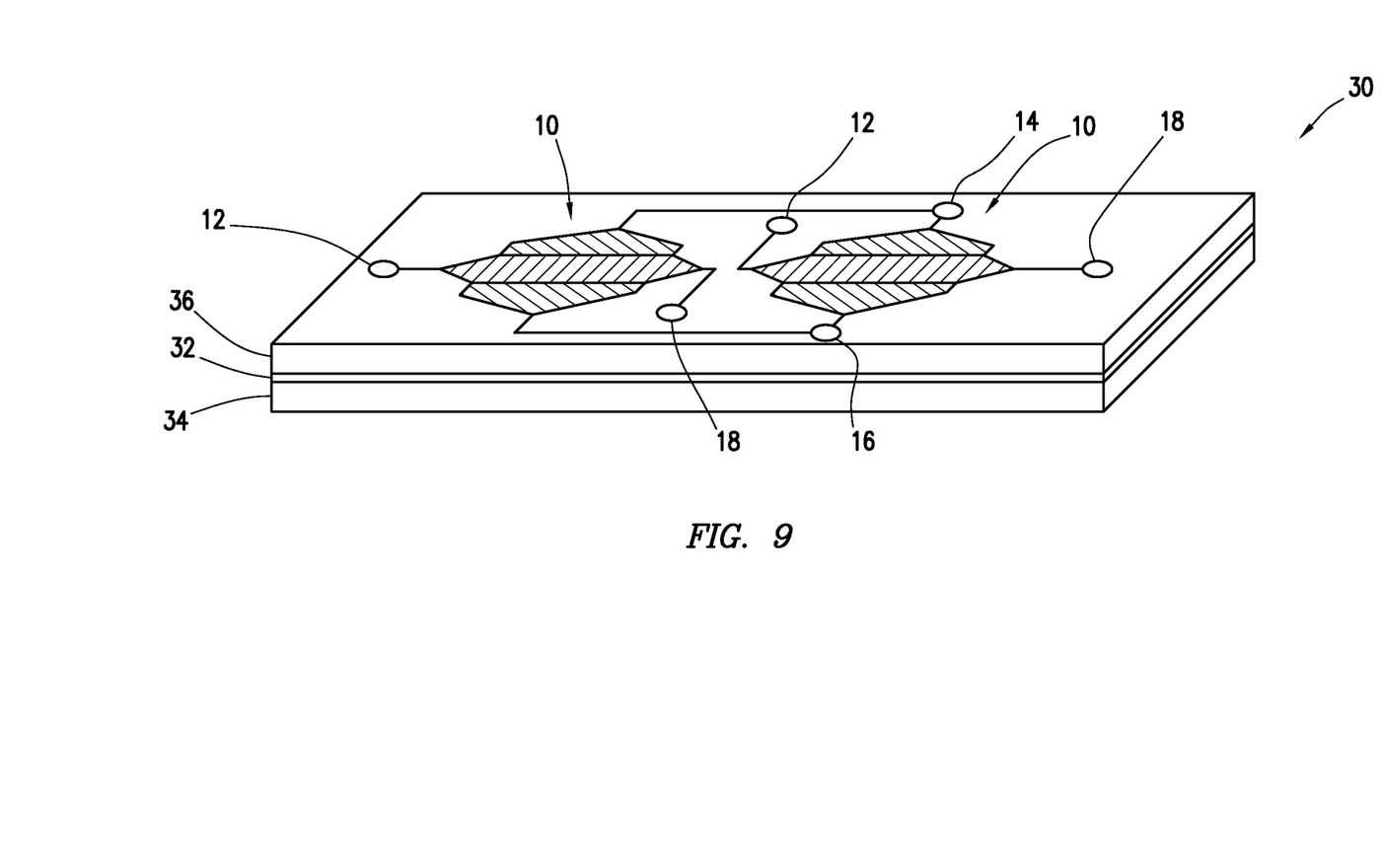
FIG. 9 depicts multiple sets of flow paths formed in a substrate according to certain embodiments.

Referring now to FIG. 9, this figure indicates that multiple flow passage 10 configurations can be formed in a single body 36 to provide flexibility in performing simultaneous testing of multiple material configurations. FIG. 9 shows two sets of flow passages 10 formed in the single body 36. However, the single body 36 can contain as many as 384 sets or more of flow passages 10 to facilitate high throughput testing. The flow paths 38, 39, 40, 41 (see FIG. 2) of each of the multiple flow passages 10 can be connected as desired either integral to the body 36, or external of the body 36, or combinations thereof. Multiple devices 30 may also be connected in either parallel, series or a combination of both to facilitate high-throughput testing for testing the various materials and fluids to determine the best treatment system including treatment fluids and possible proppant (if used) to best stimulate and/or fracture the earth formation material 60 in zone 68 of the wellbore.

Therefore, the present system is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. As used herein, the words "comprise," "have," "include," and all grammatical variations thereof are each intended to have an open, non-limiting meaning that does not exclude additional elements or steps. While compositions and methods are described in terms of "comprising," "containing," or "including" various components or steps, the compositions and methods also can "consist essentially of" or "consist of" the various components and steps. It should also be understood that, as used herein, "first," "second," and "third," are assigned arbitrarily and are merely intended to differentiate between two or more additives, etc., as the case may be, and does not indicate any sequence. Furthermore, it is to be understood that the mere use of the word "first" does not require that there be any "second," and the mere use of the word "second" does not require that there be any "third," etc.

Whenever a numerical range with a lower limit and an upper limit is disclosed, any number and any included range falling within the range is specifically disclosed. In particular, every range of values (of the form, "from about a to about b," or, equivalently, "from approximately a to b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A fluidic device that emulates a fracture in a subterranean earth formation, the device comprising:
   a body;
   a first region that emulates the fracture;
   a second region that emulates an earth formation material, wherein the first region and the second region are contained within the body of the device, and wherein the first region is in fluid communication with the second region;
   a first port that is in fluid communication with the first region; and
   a second port that is in fluid communication with the second region,
   wherein a test treatment fluid, at a test temperature and pressure, flows into the device through the first port, and at least a portion of the test treatment fluid flows out of the device, and
   wherein the test pressure is elevated above a pressure that is representative of conditions at a predetermined downhole location in the subterranean earth formation, and wherein the test temperature is elevated to a temperature that is representative of temperatures at the predetermined downhole location.

2. The device according to claim 1, wherein the test treatment fluid is analyzed as it flows into and out of the device and at least one of a parameter of the device and a characteristic of the test treatment fluid is modified in response to the analysis.

3. The device according to claim 2, wherein an actual treatment fluid is prepared based on the test treatment fluid, and the modified parameter and/or characteristic, and the actual treatment fluid is injected into a wellbore.

4. The device according to claim 3, wherein the analysis of the test treatment fluid and the preparation of the actual treatment fluid is performed on-site at the wellbore.

5. The device according to claim 1, wherein the first region emulates a proppant material that at least partially fills the fracture.

6. The device according to claim 1, wherein the first region is formed by a process selected from the group consisting of lithography, etching, 3D printing, 3D powder printing, cutting, milling, stamping, and combinations thereof, to emulate a proppant material that at least partially fills the fracture.

7. The device according to claim 6, wherein an automated selection system selects a desired parameter of the first region based on representative parameters of the proppant, wherein the parameter of the first region comprises fracture dimensions, and/or proppant type, and wherein the first region is then formed using the selected process.

8. The device according to claim 1, wherein the second region is filled with an earth formation material.

9. The device according to claim 1, wherein the second region is formed by a process selected from the group consisting of lithography, etching, 3D printing, 3D powder printing, cutting, milling, stamping, and combinations thereof, to emulate the earth formation material.

10. The device according to claim 1, wherein the device further comprises a third region that is filled with an earth formation material and is in fluid communication with the first region, and wherein the first region is positioned between the second and third regions.

11. The device according to claim 1, wherein the device further comprises a third region that is formed by a process selected from the group consisting of lithography, etching, 3D printing, 3D powder printing, cutting, milling, stamping, and combinations thereof, to emulate the earth formation material, wherein the third region is in fluid communication with the first region, and wherein the first region is positioned between the second and third regions.

12. The device according to claim 11, wherein the device further comprises third and fourth ports, and wherein the third port is in fluid communication with the third region and the fourth port is in fluid communication with the first region at an opposite side of the first region from the first port.

13. The device according to claim 12, wherein a test formation fluid that is representative of a formation fluid in the subterranean earth formation at a predetermined downhole location is supplied to the second and third ports at a representative formation pressure that is less than the test pressure, and wherein the test formation fluid flows into the second and third ports when the test pressure is reduced below the representative formation pressure.

14. The device according to claim 12, wherein a test formation fluid that is representative of a formation fluid in the subterranean earth formation at a predetermined downhole location is supplied to the second and third ports at a representative formation pressure that is less than the test pressure, whereby the test treatment fluid flows into the device through the first port at the test pressure that is elevated above the representative formation pressure, and at least a portion of the test treatment fluid flows out of the device through the fourth port when flow through the first port is prevented.

15. The device according to claim 14, wherein the test treatment fluid flowing from the first port to the fourth port is analyzed, and wherein an actual treatment fluid is prepared based on the analysis.

16. The device according to claim 1, wherein the device comprises multiple sets of at least first and second regions and at least first and second ports that are operated simultaneously with the multiple sets being included within the body, wherein at least two of the multiple sets have different flow characteristics in at least one of the first region, the second region, or a third region regions of each of the two devices.

17. The device according to claim 1, wherein the device further comprises a fourth region that is positioned between the first port and the first region, whereby the test treatment fluid flows through the fourth region when the test treatment fluid flows from the first port to the first region.

18. The device according to claim 17, wherein the fourth region emulates adsorption characteristics of the earth formation material.

19. A method of emulating fluid flow through a fracture in a subterranean earth formation, the method comprising:
   constructing a fluidic device that comprises:
   (A) a body;
   (B) a first region that emulates the fracture; and
   (C) a second region that emulates an earth formation material;
   flowing a test treatment fluid at a test temperature and pressure into the first region via a first port, thereby substantially filling the first region with the test treatment fluid, wherein the test pressure is elevated above a pressure that is representative of conditions at a predetermined downhole location in the subterranean earth formation, and wherein the test temperature is representative of a temperature at the predetermined downhole location; and reducing the test pressure at the first port, thereby allowing at least a portion of the test treatment fluid to flow out of the device.

20. The method according to claim 19, further comprising analyzing the flow of the test treatment fluid into and out of the device; and preparing an actual treatment fluid in response to the analysis.

21. The method according to claim 20, further comprising injecting the actual treatment fluid in a wellbore.

22. The method according to claim 19, wherein the first region emulates a proppant material that at least partially fills the fracture.

23. The method according to claim 19, wherein the second region is filled with an earth formation material.

24. The method according to claim 19, wherein the first and second regions are formed by a process selected from the group consisting of lithography, etching, 3D printing, 3D powder printing, cutting, milling, stamping, and combinations thereof.

25. The method according to claim 19, wherein the device further comprises a third region that is filled with an earth formation material and is in fluid communication with the first region, wherein the first region is positioned between the second and third regions, wherein a test formation fluid that is representative of a formation fluid in the subterranean earth formation at the predetermined downhole location is supplied to the second and third regions via second and third ports, respectively, and wherein the test formation fluid is supplied at the representative formation pressure.

26. The method according to claim 25, further comprising flowing the test formation fluid into the device via the second and third ports when the test pressure is reduced.

27. The method according to claim 26, wherein the device further comprises a fourth port that is in fluid communication with the first region, and wherein the portion of the test treatment fluid flows out of the device through the fourth port.

28. The method according to claim 19, wherein the device further comprises a fourth region that is positioned between the first port and the first region, whereby the test treatment fluid flows through the fourth region when the test treatment fluid flows from the first port to the first region.

29. The device according to claim 28, wherein the fourth region emulates adsorption characteristics of the earth formation material.

30. A method of emulating fluid flow through a fracture in an earth formation material surrounding a wellbore, the method comprising:

constructing a fluidic device that comprises:
(A) a body;
(B) a first region that emulates the fracture;
(C) second and third regions that emulate flow channels in the earth formation material;
(D) a fourth region that emulates adsorption characteristics of the earth formation material;

flowing a test treatment fluid at a test temperature and pressure into the device via a first port, through the fourth region, and into the first region, thereby substantially filling the first, second, and third regions with the test treatment fluid, wherein the test pressure is elevated above a pressure that is representative of conditions at a predetermined downhole location in the subterranean earth formation, and wherein the test temperature is representative of temperatures at the predetermined downhole location;

supplying a representative formation fluid to the second and third regions via second and third ports, respectively;

creating a desired backpressure in the device by preventing fluid from flowing out of the device via a fourth port positioned on a side of the first region opposite from the first port;

then permitting fluid flow from the device via the fourth port, and analyzing the fluid that flows from the fourth port;

analyzing the adsorption by the fourth region of additives in the test treatment fluid; and creating an actual treatment fluid based on the results of the analyzing steps.

* * * * *